United States Patent

Thami

[11] Patent Number: 5,200,541
[45] Date of Patent: * Apr. 6, 1993

[54] NON-CENTROSYMMETRIC ORGANOMETALLIC MOLECULES, PROCESS OF PREPARATION AND APPLICATION IN NONLINEAR OPTICS AND INTERMEDIATES

[75] Inventor: Thierry Thami, Paris, France

[73] Assignee: Societe Francaise Hoechst, Puteaux, France

[*] Notice: The portion of the term of this patent subsequent to Dec. 17, 1992 has been disclaimed.

[21] Appl. No.: 819,540

[22] Filed: Jan. 10, 1992

[30] Foreign Application Priority Data

Jan. 10, 1991 [FR] France .................. 91 00238

[51] Int. Cl.$^5$ .................. C07F 1/08; C07F 15/04; C07F 15/06; C07G 281/00
[52] U.S. Cl. .................. 556/110; 556/136; 564/227; 564/251; 359/321
[58] Field of Search ............ 556/110, 136; 564/227, 564/251; 359/321

[56] References Cited

U.S. PATENT DOCUMENTS

| | | | |
|---|---|---|---|
| 4,807,968 | 2/1989 | Leslie | 350/311 |
| 4,885,113 | 12/1989 | Gillberg-LaForce et al. | 252/582 |
| 5,035,839 | 7/1991 | Dorsch et al. | 252/587 |
| 5,119,228 | 6/1992 | Fang | 359/245 |

FOREIGN PATENT DOCUMENTS 0162804 11/1985 European Pat. Off. .

OTHER PUBLICATIONS

Chemical Abstracts, vol. 96, No. 19, May 10, 1982, p. 678, Abstract No. 161862e, Columbus, Ohio, US; B. E. Zaitzev et al.: "Synthesis and study of ligands containg a hydrazone group". VIII. Structure of glyoxal imine hydrazones & Zh. Obshch. Khim. 1982. vol. 52, No. 1 pp. 49–58.
Chemical Abstracts, vol. 94, No. 6, Feb. 9, 1981, p. 445, Abstract No. 37300q, Columbus, Ohio, US: K. P. Balakrishnan et al.: "Mode of coordination and chemical reactivity of alpha-imine hydrazone ligands" & J. Coord. Chem. 1980, vol. 10, No. 3, pp. 181–186.
Chemical Abstracts, vol. 92, Jun. 16–30, 1980, p. 681, Abstract No. 208144g, Columbus, Ohio, U.S.; K. P. Balakrishnan et al.: "Coordination behavior of imino hydrazone ligands towards nikcel (III) and copper (II) ions." & Synth. React. Inorg. Met. -Org. Chem. 1980, vol. 10, No. 1, pp. 73–81.

Primary Examiner—José Dees
Assistant Examiner—Porfirio Nazario
Attorney, Agent, or Firm—Browdy and Neimark

[57] ABSTRACT

The products having general formula (I)

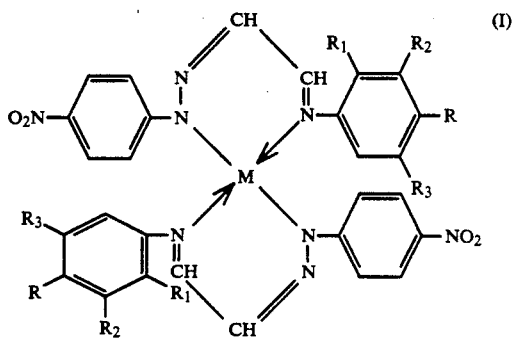

in which R represents a $C_1$–$C_{18}$ alkoxyl, $C_1$–$C_{18}$ alkylthio, $C_1$–$C_{18}$ monoalkylamino or $C_2$–$C_{36}$ dialkylamino group, $R_1$ represents a hydrogen atom or a $C_1$–$C_{18}$ alkyl group, $R_2$ and $R_3$, identical or different, represent a hydrogen atom or a $C_1$–$C_{18}$ alkoxyl group and M represents a cobalt, nickel or copper atom, process of preparation, intermediates and use of the intermediates in order to obtain a product having general formula (I).

15 Claims, No Drawings

NON-CENTROSYMMETRIC ORGANOMETALLIC MOLECULES, PROCESS OF PREPARATION AND APPLICATION IN NONLINEAR OPTICS AND INTERMEDIATES

The present invention relates to new noncentrosymmetric organometallic molecules, a process for the preparation thereof and their application in nonlinear optics and intermediates.

It is known that, in order to obtain a material which is active in nonlinear optics, it is advisable to use molecules having strong beta molecular hyperpolarizability, $\beta$, then to organise them according to a non-centrosymmetric arrangement.

Thus it is known to use non-centrosymmetric organic molecules bearing conjugated donor and acceptor groups of which the $\beta ijk$ coefficients are generally uniaxial and which have standardised values $\beta 0$, independent of the frequency, of the order of 5 to 70 $10^{-30}$ electrostatic units (e.s.u.), such as in particular stilbene derivatives. In these known molecules, the principal nonlinear optical effect is observed in the direction of the axis of charge transfer which generally coincides with their permanent dipole moment. These molecules are organized either by orientation with the aid of an electric field or by formation of monocrystals or Langmuir-Blodgett layers so as to promote their non-centrosymmetric alignment.

In nonlinear optics, however, molecules are sought which have strong hyperpolarizability in several directions in space having in particular high and preferably chiral non-diagonal hyperpolarizability coefficients. The formation of molecular materials from one of the optical isomers would then lead to a non-centrosymmetric condensed phase.

Now the applicant has discovered chiral organo-metallic molecules exhibiting strong hyperpolarizability in several directions in space.

The organometallic formulae according to the present invention are products having general formula (I)

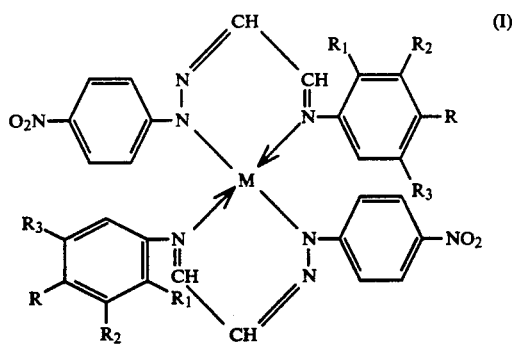

(I)

in which R represents a $C_1$-$C_{18}$ alkoxyl, $C_1$-$C_{18}$ alkylthio, $C_1$-$C_{18}$ monoalkylamino or $C_2$-$C_{36}$ dialkylamino group, $R_1$ represents a hydrogen atom or a $C_1$-$C_{18}$ alkyl group, $R_2$ and $R_3$, identical or different, represent a hydrogen atom or a $C_1$-$C_{18}$ alkoxyl group and M represents a cobalt, nickel or copper atom.

The $C_1$-$C_{18}$ alkoxyl group can be, for example, a methoxyl, ethoxyl, n-propoxyl, n-butoxyl, hexyloxyl, octyloxyl, dodecyloxyl, octadecyloxyl, preferably n-propoxyl or ethoxyl, particularly methoxyl radical.

The $C_1$-$C_{18}$ alkylthio group can be, for example, an ethylthio, n-propylthio, n-butylthio, n-hexylthio, n-octylthio, n-dodecylthio, n-octadecylthio, preferably methylthio radical.

The $C_1$-$C_{18}$ alkyl group can be, for example, a methyl, ethyl, n-propyl, n-butyl, n-hexyl, n-octyl, n-dodecyl, n-octadecyl, preferably n-propyl or ethyl and quite particularly methyl radical.

The expression $C_1$-$C_{18}$ monoalkylamino can designate, for example, a methylamino, ethylamino, butylamino, preferably methylamino group.

The expression $C_2$-$C_{36}$ dialkylamino can designate, for example, a dimethylamino, diethylamino, N-methyl N-ethylamino, dipropylamino, dibutylamino, preferably dimethylamino group.

Amongst the molecules having general formula (I), the subject of the invention is more particularly the products in which R, $R_1$, $R_2$, $R_3$ and M have the meaning given in table (I) below.

TABLE 1

| No. | R | $R_1$ | $R_2$ | $R_3$ | M | Empirical formula |
|---|---|---|---|---|---|---|
| 1 | OMe | H | H | H | Cu | $C_{30}H_{26}N_8O_6Cu$ |
| 2 | OMe | H | H | H | Ni | $C_{30}H_{26}N_8O_6Ni$ |
| 3 | OMe | H | H | H | Co | $C_{30}H_{26}N_8O_6Co$ |
| 4 | SMe | H | H | H | Co | $C_{30}H_{26}N_8O_4S_2Co$ |
| 5 | N(Me)$_2$ | H | H | H | Co | $C_{32}H_{32}N_{10}O_4Co$ |
| 6 | OMe | H | OMe | OMe | Co | $C_{34}H_{34}N_8O_{10}Co$ |
| 7 | OMe | Me | H | H | Co | $C_{32}H_{30}N_8O_6Co$ |

In the products having general formula (I), the metal M is tetracoordinated with the nitrogen atoms linked to the aromatic nuclei. It has been possible to show by X ray diffraction of product 5 that the structure of the complex is of the tetrahedral type. It is deduced from this, when M represents a cobalt atom, that the products having general formula (I) are chiral. However, in the case of product 5, the monocrystal for its part is composed of a racemic mixture and the latter is centrosymmetric (cf. table XI below).

The subject of the present invention is also a process for the preparation of the products having general formula (I). According to the invention, the products having general formula (I) can be prepared by a process characterized in that a product having general formula (II)

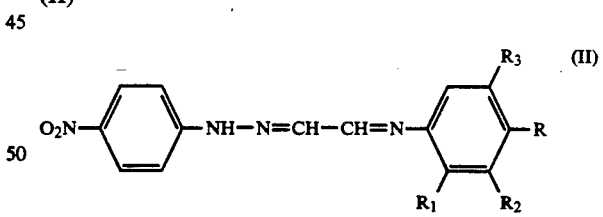

(II)

in which R, $R_1$, $R_2$, $R_3$ have the meaning given previously, is allowed to react, preferably in the presence of an alkaline agent, with a metal salt or complex having general formula (III)

M(A)$_2$ (III)

in which M has the meaning given previously and A represents the acetylacetonate radical designated AcAc or the anionic radical of a mineral or organic acid, in order to obtain a corresponding product having general formula (I).

The anionic radical of a mineral or organic acid can be, for example, an acetoxyl, nitrate, bromide or triflate ion.

Under preferential operating conditions, the process described above is carried out at a temperature between 20° C. and 80° C., in an anhydrous polar solvent, in the presence of a slight excess of product having general formula (III) and in an anhydrous medium.

The alkaline agent used is chosen from the conventional anhydrous bases such as the sodium, potassium or lithium $C_1$–$C_2$ alcoholates or the tertiary amines such as, for example, triethylamine.

The reaction solvent used is chosen preferably from the anhydrous polar solvents, advantageously from those dissolving the reaction reagents and in which the expected product is sparingly soluble and even insoluble. The reaction solvent is preferably methanol or ethanol.

The metal salts or complexes having general formula (III) are commercial products and they are chosen preferentially in terms of their solubility in anhydrous polar solvents. Advantageously, the product having general formula (III) is chosen from the following products: copper II acetate, cobalt II acetate, nickel II bromide, nickel II acetylacetonate, copper II triflate. If these commercial products are crystallized with water, the latter is carefully removed by drying under reduced pressure at 150° C.

The products having general formula (II) are generally described and they can be obtained in particular from known products by known processes such as, for example, condensation of glyoxal monoparanitrophenylhydrazone, described by G. V. SHANDURENKO et al. Zh. Org. Khim., 1980, 16, 751–754, with the corresponding aniline as taught in particular by B. CHISWELL et al, Inorg. Chim. Acta, 1979, 35, 141–148. But certain products having general formula (II) are new. Thus the condensation of glyoxal monoparanitrophenylhydrazone, hereinafter known as NPHG, with paramethylmercaptoaniline gives paranitrophenylhydrazono-1 paramethylphenylimino-2 ethane, 8.

Similarly, the condensation of NPHG with either paradimethylaminoaniline or trimethoxy-3,4,5 aniline or finally methyl-2 methoxy-4 aniline gives paranitrophenylhydrazono-1 paradimethylaminophenylimino-2 ethane, 9, paranitrophenylhydrazono-1 (trimethoxy-3,4,5 phenyl)imino-2 ethane, 10, and paranitrophenylhydrazono-1 (methyl-2 methoxy-4 phenyl)imino-2 ethane, 11, respectively. To the knowledge of the applicant, products 8, 9, 10 and 11 are not described in the literature. They bring essential components to the products having formula (I) described above. For that reason, the subject of the present invention is also such products having formula (II).

The products having general formula (II) have an acid character, and with bases they yield generally crystallized salts. As a result, in the process described above, the stoichiometric quantity of base is generally used in order to convert entirely to a salt the product having formula (II) employed.

According to a variant of the process according to the invention, the product having general formula (II) can be used in the form of an anhydrous crystallized salt and in this case the process of the invention is carried out in the absence of an alkaline agent.

The products having general formula (II) possess in their structure a system of conjugated ethylenic bonds: they have therefore potential s-cis and s-trans isomerism. These two conformers are, moreover, associated with potential E and Z configurational isomerism of the sp2 nitrogen atoms. In theory, there are four configurational isomers for each conformer, designated (E′E), (E′Z), (Z′E) and (Z′Z). In solution it has been possible to show by proton NMR that the products having general formula (II) adopt the two s-trans and s-cis conformations. In accordance with the E′-s-trans-E structure of ligand 9 determined by X ray diffraction on a monocrystal and with the bibliographic data, it is probable that the products having general formula (II) exist in solution in two majority isomer forms: the linear E′-s-trans-E form and the chelated Z′-s-cis-E form. In the products having general formula (I), the corresponding ligands having general formula (II) adopt the Z′-s-cis-E configuration.

The products having general formula (I) have astonishing properties in nonlinear optics. In solution in solvents such as dioxane or chloroform, the products having general formula (I) have high values of field-induced second harmonic generation determined by EFISH measurement (Electric Field Induced Second Harmonic) at a wave length of the incident beam $\lambda = 2\pi c/\omega$ of 1.9 μm. Moreover, the products having general formula (I) have dipole moments, designated μ, of the order of 11 to 14 debye. Assuming a tetrahedral arrangement and the additive nature of the dipole moments of the ligands, the dipole moments of the products having general formula (I) are consistent with theory.

In table II we give the results of the measurements of second harmonic generation by the EFISH method on the products having general formula (I) and (II) in $10^{-2}$ to $10^{-3}$ M solution in dioxane or chloroform at 25° C., according to M. BARZOUKAS et al, J. Opt. Soc. Amer. B, 1987, 84, 977. These values were measured in the laboratory of Professor VILLAEYS in Strasbourg.

Thus in table II we give the value of the mean microscopic hyperpolarizability coefficient, γo, expressed in electrostatic units, as well as $\mu_z$, $\beta_z^\omega$ expressed in e.s.u. where the z axis coincide the permanent dipole moment of the molecule (thus $\|\vec{\mu}\| = \mu = \mu_z$) and $\beta_z^\omega$ is the vector component on the z axis of the molecular hyperpolarizability tensor $\beta^\omega ijk$, i.e.:

$$\beta_z^{2\omega} = \tfrac{1}{3}(3\beta_{zzz}^{2\omega} + \beta_{zxx}^{2\omega} + \beta_{zyy}^{2\omega} + 2\beta_{xxz}^{2\omega} + 2\beta_{yyz}^{2\omega})$$

for polar molecules such as the products having general formula (I) and (II), the coefficient 7° obtained by the EFISH method is linked to the molecular parameters $\mu_z \beta_z^\omega$ by the equation:

$$\gamma^o = \gamma^c + \mu_z\beta_z^\omega/5kT$$

where k represents the Boltzmann constant and T the absolute temperature. Given that the products having general formula (I) and (II) are non-centrosymmetric molecules in which the donor and acceptor groups are linked by highly conjugated subunits, the electronic term $\gamma^c$ can be ignored ($\gamma^c$ is the scalar part of the molecular hyperpolarizability tensor γijkl).

The preceding equation can therefore be written:

At an experimental temperature of 25° C., the equation is:

$$\mu_z \mu_z^\omega = 2.06 \; 10^{-12} \gamma^o$$

By way of comparison, we also give in table II the results of the EFISH measurements carried out on ligands 8, 9, 10 and 12 which are generators of products of 4, 5, 6 and 3.

TABLE II

Results of the EFISH measurements

EFISH measurements at $\lambda = 1.9 \, \mu m \left( \lambda = \frac{2\pi C}{\omega} \right)$

| | DIOXANE | | CHLOROFORM | |
|---|---|---|---|---|
| No. | $\gamma o$ $10^{-36}$ e.s.u. | $\mu_z \beta_z^{2\omega}$ $10^{-48}$ e.s.u. | $\gamma o$ $10^{-36}$ e.s.u. | $\mu_z \beta_z^{2\omega}$ $10^{-48}$ e.s.u. |
| 12 | 770 | 160 | 580 | 120 |
| 9 | 1980 | 410 | 2000 | 415 |
| 8 | 480 | 100 | 725 | 150 |
| 10 | 360 | 75 | 360 | 75 |
| 3 | 1500 | 310 | 1600 | 330 |
| 5 | 4590 | 950 | 7000 | 1450 |
| 4 | 1930 | 400 | 2170 | 450 |
| 6 | 1450 | 300 | 1210 | 250 |
| 7 | 1400 | 390 | 1930 | 400 |

TABLE IIb

Permanent electric dipole moments of the products having general formula (I) and (II)

| | $\mu$ (Debye) | | |
|---|---|---|---|
| No. | dioxane | chloroform | benzene |
| 12 | 6.35 | 10.2 | |
| 9 | 8.25 | 8.2 | |
| 3 | 12.1 | 10.0 | 11.2 |
| 5 | 13.6 | 12.6 | |

The percentage by weight of Z'-s-cis-E and E'-s-trans-E isomers present in solution in the solvent chosen are brought into the calculations for determining $\beta_z^{2\omega}$ for the product having general formula (II) studied. This percentage is determined by proton NMR at 25° C. at equilibrium in the same solvent (cf. table VII c). The values of the dipole moments of the products having general formula (I) and (II) are given in table II b). These values were determined according to G. M. JANINI et al, J. Chem. Educ, 1983, 60 (12), 1087, in $10^{-2}$ to $10^{-3}$ M solution in dioxane, chloroform and benzene at 25° C. at a frequency of I kHz. The measurements carried out in chloroform were corrected according to C. F. BOTTCHER, Theory of Electric Polarization, Elsevier, Amsterdam, 1978:

$$\mu \text{ corrected} = \mu \text{ measured} \frac{(\epsilon o + 2)(\epsilon \infty + 2\epsilon o)}{3\epsilon o (\epsilon \infty + 2)}$$

where $\epsilon o$ represents the static dielectric constant and $\epsilon \infty$ the high frequency dielectric constant of the solvent. In the case of chloroform $\epsilon o = 4.8$ and $\epsilon \infty = 3$, so the correction factor is 1.19.

By way of example, at $\lambda = 1.9 \, \mu m$, complex 5 has a value of $\beta_z^\omega$ equal to $115 \, 10^{-30}$ e.s.u. and product 9 has a value $\beta_z^\omega$ equal to $50 \, 10^{-30}$ e.s.u.

For product 9, the experimental values $\beta_z^\omega$ and the values calculated for the Z'-s-cis-E and E'-s-trans-E isomers are close. The products having general formula (I) have greatly increased non-diagonal coefficients in comparison with the corresponding ligand having general formula (II).

In table III we give the ultraviolet, visible and near infrared absorption characteristics of the products having general formula (I) in solution in dichloromethane. In this table the wave lengths are expressed in nm and the extinction coefficients, $\epsilon$, in mole$^{-1}$ dm$^3$ cm$^{-1}$.

TABLE III

| No. | $\lambda$ max ($\epsilon$ max) solvent: dichloromethane | | | | | |
|---|---|---|---|---|---|---|
| 1 | 465 | (39700) | 679 | (2490) | 1330 | (210) |
| 2 | 461 | (46300) | 650* | (2500) | 1110 | (47) |
| 3 | 478 | (54200) | 690 | (2450) | 1020 | (77) |
| 4 | 479 | (58300) | 693 | (2850) | 1020 | (82) |
| 5 | 518 | (53800) | 670* | (2950) | 1020 | (74) |
| 6 | 477 | (50000) | 685 | (2390) | 1020 | (76) |
| 7 | 469 | (42900) | 688 | (2100) | 1030 | (80) |

*shoulder: the maximum of the band is masked by the more intense adjacent band.

In table IV we give the ultraviolet and visible absorption characteristics of the products having general formula (II) in solution in ethanol in a neutral and in a basic medium.

TABLE IV

| | Neutral medium | | Basic medium | |
|---|---|---|---|---|
| No. | $\lambda$ max in nm | ($\epsilon$ max) | $\lambda$ max in nm | ($\epsilon$ max) |
| 8 | 410 | (52400) | 557 | (52400) |
| 9 | 436 | (47800) | 565 | (55600) |
| 10 | 406 | (48400) | 555 | (54500) |
| 11 | 407 | | 549 | |
| 12 | 404 | (41500) | 552 | (45200) |

The following examples illustrate the invention yet without limiting its scope.

EXAMPLE 1

A solution of 37.5 g (245 mmoles) of paranitrophenylhydrazine dissolved in 1050 g of acetic acid is introduced in 40 min., with agitation, at ambient temperature, into an aqueous solution of 21.28 g (366 mmoles) of glyoxal dissolved in 1280 g of water.

The glyoxal monoparanitrophenylhydrazone sought crystallizes immediately in the reaction medium in the form of red crystals.

At the end of introduction, the reaction medium is left for 2 hours at ambient temperature with agitation, then the precipitate is filtered and then washed with water then dried at 60° C. under reduced pressure to a constant weight. 44 g (228 mmoles) of glyoxal monoparanitrophenylhydrazone are obtained in this way, i.e. a yield of 93% of the theoretical calculated with respect to the paranitrophenylhydrazine used. This product is described in the literature (G. V. SHANDURENKO et al, Zhu. Obsh. Khim. 1980, 50, 2259-2263).

123 mg (1 mmole) of paraanisidine dissolved in 3 g of ethanol are introduced in 10 minutes with agitation into a reflux solution of 193 mg (1 mmole) of glyoxal monoparanitrophenylhydrazone in 16 g of ethanol. The solution obtained is then cooled to ambient temperature, the product sought crystallizes spontaneously, it is centrifuged then dried to a constant weight under reduced pressure at 60° C. 123 mg (0.41 mmole) of paramethoxyphenylimino-Iparanitro-phenylhydrazino-2 ethane, 12, are obtained in this way, crystallized in the form of orange needles having a melting point of 252±2° C. The yield is 41% of the theoretical.

This product is described in the literature: G. V. SHANDURENKO et al, Zh. Org. Khim, 1980, 16, 751-754 MP=209-210° C.

EXAMPLES 2-5

Operating as in example but replacing paraanisidine by an equivalent quantity either, of paramethylmercaptoaniline or paradimethylaminoaniline, or trimethoxy- 3,4,5 aniline, or finally methyl-2 methoxy-4 aniline, paraitrophenylhydrazono-1 paramethylmercaptophenylimino-2 ethane, 8, paranitrophenylhydrazono-1 paradimethylaminophenylimino-2 ethane, 9, paranitrophenylhydrazono-1 (trimethoxy-3,4,5 phenyl)imino-2 ethane, 10, paranitrophenylhydrazono-1 (methyl-2 methoxy-4 phenyl)imino-2 ethane, respectively are obtained.

The characteristics of these products are given in tables IV, V, VI, VII, VIIb) and VIIc).

TABLE V

Elemental analyses and melting points of the products having general formula (II)

| No. | Empirical formula | M.W. | | Elemental analysis (% by wt) | | | | M.P. |
|---|---|---|---|---|---|---|---|---|
| 8 | $C_{15}H_{14}N_4O_2S$ | 314.37 | calculated: | C: 57.31 | H: 4.49 | N: 17.82 | S: 10.20 | 246° C. |
| | | | found: | C: 56.7 | H: 4.4 | N: 17.8 | S: 10.0 | |
| 9 | $C_{16}H_{17}N_5O_2$ | 311.34 | calculated: | C: 61.72 | H: 5.50 | N: 22.49 | | 261° C. |
| | | | found: | C: 61.8 | H: 5.5 | N: 22.4 | | |
| 10 | $C_{17}H_{18}N_4O_5$ | 358.36 | calculated: | C: 56.98 | H: 5.06 | N: 15.63 | | 243° C. |
| | | | found: | C: 56.84 | H: 5.02 | N: 15.51 | | |
| 11 | $C_{16}H_{16}N_4O_3$ | 312.33 | calculated: | C: 61.53 | H: 5.16 | N: 17.94 | | |
| | | | found: | C: | H: | N: | | |
| 12 | $C_{15}H_{14}N_4O_3$ | 298.30 | calculated: | C: 60.40 | H: 4.73 | N: 18.78 | | 252° C. |
| | | | found: | C: 60.19 | H: 4.64 | N: 18.52 | | (lit. 209–210° C.) |

TABLE VI $^1$H NMR of the products having general formula (II) in DMSO-$d^6$

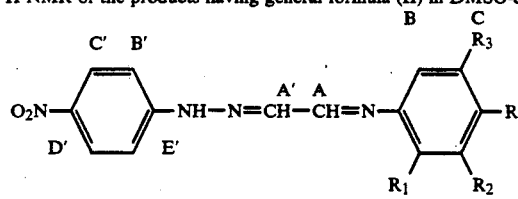

| No | C' | (J B'C') | B' | NH | A' | (J A'A) | A | B | (J BC) | C | R |
|---|---|---|---|---|---|---|---|---|---|---|---|
| 8 | 8.22 | (9.2 Hz) | 7.25 | 11.8 | 7.88 | (8.2 Hz) | 8.40 | 7.32 | (singlet) | | 2.53 |
| 9 | 8.18 | (9.2 Hz) | 7.19 | 11.65 | 7.83 | (8.1 Hz) | 8.38 | 7.29 | (9.0 Hz) | 6.73 | 2.93 |
| 10 | 8.19 | (9.0 Hz) | 7.21 | 11.7 | 7.83 | (8.2 Hz) | 8.41 | 6.66 | (singlet) | | 3.82 meta |
| | | | | | | | | | | | 3.67 para |
| 12 | 8.18 | (9.2 Hz) | 7.21 | 11.7 | 7.83 | (8.1 Hz) | 8.37 | 7.33 | (8.8 Hz) | 6.96 | 3.78 |

Remark:
- the configuration of the products in this solvent is E'-s-trans-E.
- the chemical shifts are given in ppm with respect to TMS
- the assignment of the protons is given for guidance.

TABLE VII $^{13}$C NMR of the products having general formula (II) in DMSO-$d^6$

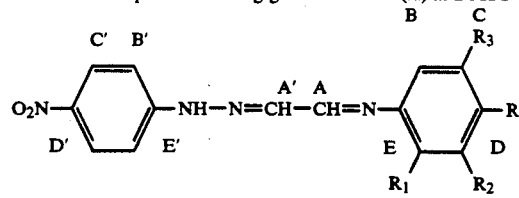

| No. | D' | C' | B' | E' | A' | A | E | B | C | D | R |
|---|---|---|---|---|---|---|---|---|---|---|---|
| 8 | 139.8 | 126.6 | 112.2 | 149.2 | 141.6 | 165.9 | 147.3 | 125.9 | 121.7 | 136.5 | 14.8 |
| 9 | 139.4 | 126.1 | 112.0 | 149.6 | 142.9 | 151.9 | 149.8 | 122.7 | 112.4 | 138.8 | 40.4 |
| 10 | 139.9 | 126.0 | 112.3 | 149.4 | 141.8 | 157.1 | 136.6 | 99.0 | 153.2 | 146.1 | 60.1 para |
| | | | | | | | | | | | 56.0 meta |
| 12 | 141.9 | 125.9 | 112.0 | 149.3 | 143.1 | 158.3 | 155.3 | 122.5 | 114.3 | 139.5 | 55.1 |

- the chemical shifts are given in ppm with respect to TMS
- the assignment of the carbons is given for guidance.

TABLE VIIb $^1$H NMR characteristics (*) of the E'-s-trans-E and Z'-s-cis-E isomers of the products having general formula (II)

| | E'-s-trans-E ISOMER | | | | Z'-s-cis-E ISOMER | | | |
|---|---|---|---|---|---|---|---|---|
| No. | A' | (J A'A) | A | NH trans | A' | (J A'A) | A | NH cis |
| 12 (a) | 7.70 | (7.7 Hz) | 8.35 | 8.4 | 7.05 | (2.1 Hz) | 8.11 | 14.7 |
| (b) | 7.83 | (8.1 Hz) | 8.35 | 11.7 | — | (not detected) | — | — |
| 8 (a) | — | — | — | — | — | — | — | — |
| (b) | 7.88 | (8.2 Hz) | 8.40 | 11.8 | — | (not detected) | — | — |
| 9 (a) | 7.70 | (7.9 Hz) | 8.37 | 8.4 | 7.01 | (1.9 Hz) | 8.12 | 14.8 |
| (b) | 7.88 | (8.2 Hz) | 8.40 | 11.8 | — | (not detected) | — | — |

TABLE VIIb-continued $^1$H NMR characteristics (*) of the E'-s-trans-E and Z'-s-cis-E isomers of the products having general formula (II)

| | E'-s-trans-E ISOMER | | | | Z'-s-cis-E ISOMER | | | |
|---|---|---|---|---|---|---|---|---|
| No. | A' | (J A'A) | A | NH trans | A' | (J A'A) | A | NH cis |
| 10 (a) | 7.69 | (8.0 Hz) | 8.36 | 8.3 | 7.07 | (2.1 Hz) | 8.07 | 14.4 |
| (b) | 7.83 | (8.2 Hz) | 8.41 | 11.7 | — | (not detected) | — | |

(a) solvent CDCl$_3$
(b) solvent DMSO-d$^6$
(*) the chemical shifts are given in ppm with respect to TMS.

TABLE VIIc

Percentages by weight of the isomers E'-s-trans-E and Z'-s-cis-E isomers of the products having general formula (II) in solution.

| | DMSO | | Acetone | | Dioxane | | CDCl$_3$ | |
|---|---|---|---|---|---|---|---|---|
| No. | % trans | % cis | % trans | % cis | % trans | % cis | % trans | % cis |
| 12 | 100 | 0 | 100 | 0 | 80 | 20 | 30 | 70 |
| 8 | 100 | 0 | 100 | 0 | 90 | 10 | | |
| 9 | 100 | 0 | 85 | 15 | 85 | 15 | 25 | 75 |
| 10 | 100 | 0 | | | 100 | 0 | 45 | 55 |

EXAMPLE 6

1 g (3.35 mmoles) of paranitrophenylhydrazono-1 paramethoxyphenylimino-2 ethane, 12, in 80 g of anhydrous ethanol is heated under reflux with agitation, then 3.35 ml of a 1M solution of potassium ethylate in ethanol, i.e. 3.35 mmoles are introduced slowly into this suspension. A violet solution is rapidly obtained. 326 mg (1.84 mmoles) of anhydrous cobalt II acetate are then introduced into this solution. The product sought crystallizes spontaneously under hot conditions. The suspension obtained, cooled to ambient temperature, is filtered then the precipitate collected is absorbed in 30 g of dichloromethane in order to remove some impurities which are insoluble in this solvent. The chloromethylenic filtrate is then concentrated to dryness under reduced pressure then the residual crystallized precipitate is recrystallized by heating and cooling in a 1:1 by volume mixture of ethyl acetate-ethanol. In this way, 0.820 g of desired product 3 crystallized into green needles is obtained, i.e. a yield of 75% of the theoretical. This product is very soluble in dichloromethane, chloroform, acetone, benzene, ethyl acetate and carbon tetrachloride.

The physical characteristics of this product are given in tables III, VIII, IX and X.

EXAMPLES 7-11

Operating as in example 6 with starting products 8, 9, 10, and 11 and in the presence of anhydrous cobalt II acetate, products 4, 5, 6 and 7 respectively are obtained in the crystalline state. The physical characteristics of these products are given in tables III, VIII, IX and X. The crystalline structure of product 5 was determined by X ray diffraction: the crystallographic data are given in table XI.

EXAMPLE 12

149 mg (0.5 mmole) of paranitrophenylhydrazono-1 paramethoxyphenylimino-2 ethane, 12 in 32 g of anhydrous ethanol are heated to 60° C. with agitation, then 0.5 ml of a 1M solution of potassium ethylate in ethanol are introduced into this suspension. A violet solution is obtained very rapidly which is cooled to ambient temperature. 90 mg (0.25 mmole) of anhydrous copper triflate Cu(F$_3$CSO$_3$)$_2$ are then introduced into this solution. The desired product crystallizes, it is centrifuged and then washed by mixing with ethanol. In this way, 121 mg of product 1 are obtained, i.e. a yield of 74%. The physical constants of this product are given in tables III, VIII, IX and X.

EXAMPLE 13

Operating as in example 12 but replacing copper triflate by an equivalent quantity of anhydrous nickel bromide, 244 mg of product 2 are obtained after recrystallization in an acetone-ethanol mixture, i.e. a yield of 20%. The physical characteristics of this product are given in tables III, VIII, IX and X.

TABLE VIII

Elemental analyses of the products having general formula (I)

| No. | Empirical formula | M.W. | | Elemental analysis (% by weight) | | | |
|---|---|---|---|---|---|---|---|
| 1 | C$_{30}$H$_{26}$N$_8$O$_6$Cu | 658.13 | calculated: | C: 54.75 | H: 3.98 | N: 17.02 | Cu: 9.65 |
| | | | found: | C: 54.58 | H: 3.92 | N: 16.90 | Cu: 9.88 |
| 2 | C$_{30}$H$_{26}$N$_8$O$_6$Ni | 653.30 | calculated: | C: 55.16 | H: 4.01 | N: 17.15 | Ni: 8.99 |
| | | | found: | C: 55.53 | H: 3.97 | N: 17.20 | Ni: 9.87 |
| 3** | C$_{30}$H$_{26}$N$_8$O$_6$Co | 653.52 | calculated: | C: 55.14 | H: 4.01 | N: 17.15 | Co: 9.02 |
| | | | found: | C: 55.31 | H: 3.96 | N: 17.16 | Co: 8.89 |
| 4* | C$_{30}$H$_{26}$N$_8$O$_4$S$_2$Co | 685.65 | calculated: | C: 52.55 | H: 3.82 | N: 16.34 | Co: 8.60 |
| | | | found: | C: 52.71 | H: 3.76 | N: 16.51 | Co: 9.68 |
| 5 | C$_{32}$H$_{32}$N$_{10}$O$_4$Co | 679.61 | calculated: | C: 56.56 | H: 4.75 | N: 20.61 | Co: 8.67 |
| | | | found: | C: 56.51 | H: 4.75 | N: 20.61 | Co: 8.57 |
| 6 | C$_{34}$H$_{34}$N$_8$O$_{10}$Co | 773.63 | calculated: | C: 52.79 | H: 4.43 | N: 14.48 | Co: 7.62 |
| | | | found: | C: 52.77 | H: 4.24 | N: 14.53 | Co: 7.81 |
| 7 | C$_{32}$H$_{30}$N$_8$O$_6$Co | 681.58 | calculated: | C: 56.39 | H: 4.44 | N: 16.44 | Co: 8.65 |

TABLE VIII-continued

Elemental analyses of the products having general formula (I)

| No. | Empirical formula | M.W. | Elemental analysis (% by weight) |
|---|---|---|---|
| | | found: | C: 56.58  H: 4.32  N: 16.15  Co: 8.88 |

*the determination of sulphur by the usual method (Schöniger) gives poor results due to interference with cobalt.
**this complex crystallizes with benzene molecules when it is purified in this solvent.

TABLE IX

Infrared spectra (KBr) of the products having general formula (I)

| No. | Number of waves in cm-1- | | | | | | | | | | | | |
|---|---|---|---|---|---|---|---|---|---|---|---|---|---|
| 1 | 1604.9 | 1585.4 | 1503.9 | 1457.2 | 1329.8 1318.1 | 1237.8 | 1159.7 | 1100.6 | 1020.0 | (—) | 846.2 | 751.2 | 692.4 |
| 2 | 1605.7 | 1585.9 | 1505.0 | 1460.8 | 1330.1 1318.3 | 1226.9 | 1152.3 | 1102.1 | 1025.6 | (—) | 845.9 | 751.5 | 693.5 |
| 3 | 1605.1 | 1586.2 | 1505.4 | 1457.8 | 1322.1 | 1231.8 | 1150.8 | 1106.4 | 1016.1 | 994.7 | 848.2 | 753.8 | 693.1 |
| 4 | (—) | 1586.0 | 1501.6 | 1454.8 | 1320.8 | 1226.6 | 1152.5 | 1107.5 | 1019.5 | 996.7 | 845.9 | 753.1 | 690.4 |
| 5 | 1607.3 | 1584.9 | 1498.4 | 1458.5 | 1319.2 | 1237.8 | 1143.9 | 1101.9 | 1021.4 | 998.1 | 849.5 | 752.9 | 693.7 |
| 6 | (—) | 1587.3 | 1507.8 | 1454.1 | 1321.1 | 1230.6 | 1127.4 | 1106.6 | 1014.0 | 996.8 | 855.2 | 753.5 | 690.5 |
| 7 | 1603.3 | 1586.7 | 1507.7 | 1457.9 | 1321.1 | 1232.4 | 1151.1 | 1105.6 | 1016.2 | 997.2 | 850.7 | 752.2 | 693.2 |

(—) shoulder

TABLE X

Calculation of the d-d metal transition bands of the products having general formula (I) according to TANABE-SUGANO diagrams.

| | |
|---|---|
| $Cu^{2+}$ ($d^9$) geometry $T_d$ 1 band | $v = \Delta_t = 7500$ cm$^{-1}$ (1330 nm) |
| $Ni^{2+}$ ($d^8$) geometry $T_d$ 3 bands | calculated (a): ($\Delta_t = 9800$ cm$^{-1}$ B = 970 cm$^{-1}$) $v_1 = 8570$ cm$^{-1}$ (1170 nm) $v_2 = 21900$ cm$^{-1}$ (455 nm) $v_3 = 18400$ cm$^{-1}$ (540 nm) |
| $Co^{2+}$ ($d^7$) geometry $T_d$ 3 bands | calculated (b): ($\Delta_t = 9800$ cm$^{-1}$ B = 980 cm$^{-1}$) $v_1 = 9800$ cm$^{-1}$ (1020 nm) $v_2 = 16150$ cm$^{-1}$ (620 nm) $v_3 = 27950$ cm$^{-1}$ (360 nm) |

The parameters B were chosen for cobalt and nickel in Inorganic Chemistry, K. F. Purcell and J. C. Kotz, Holt Saunders International Editions, Hong-Kong, 1987. The parameters $\Delta t$ were estimated from the absorption energies of the products having general formula (I) in the near infrared (cf. table III). The values $V_1$, $V_2$ and $V_c$ were calculated by means of the following theoretical expressions:

| Theoretical expressions: | |
|---|---|
| (a) $v_1 = 0.5\Delta_t - 7.5 B + Q$ $v_2 = 2Q$ $v_3 = 1.5 \Delta_t - 7.5 B + Q$ | $Q = \frac{1}{2} [225 B^2 + \Delta_t^2 + 18\Delta_t B]^{\frac{1}{2}}$ |
| (b) $v_1 = \Delta_t$ $v_2 = 1.5\Delta_t + 7.5 B + Q$ $v_3 = 1.5 \Delta_t - 7.5 B + Q$ | $Q = \frac{1}{2} [225 B^2 + \Delta_t^2 - 18\Delta_t B]^{\frac{1}{2}}$ |

TABLE XI

Crystallographic data of product 5 determined by X ray diffraction

| | |
|---|---|
| Formula | $C_{32}H_{32}N_{10}O_4Co$ |
| Mw | 679.607 |
| cryst. system | triclinic |
| space group | $\overline{P1}$ |
| a = | 1.0819 (2) nm |
| b = | 1.1645 (1) nm |
| c = | 1.3991 (2) nm |
| alpha = | 86°24' (1) |
| beta = | 84°58' (1) |
| gamma = | 70°34' (1) |
| V, Å$^3$ | 1655 (7) |
| Z | 2 |
| $\rho$ (calcd), g cm$^{-3}$ | 1.364 |

What is claimed is:

1. The products having general formula (I)

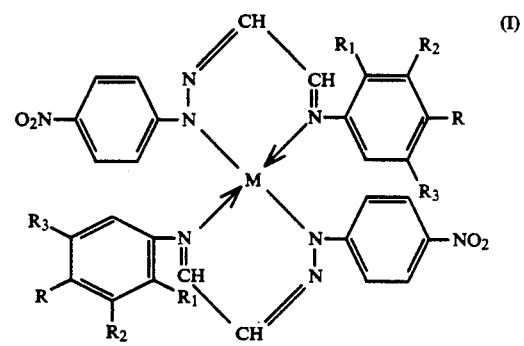

in which R represents a $C_1$-$C_{18}$ alkoxyl, $C_1$-$C_{18}$ alkylthio, $C_1$-$C_{18}$ monoalkylamino or $C_2$-$C_{36}$ dialkylamino group, $R_1$ represents a hydrogen atom or a $C_1$-$C_{18}$ alkyl group, $R_2$ and $R_3$, identical or different, represent a hydrogen atom or a $C_1$-$C_{18}$ alkoxyl group and M represents a cobalt, nickel or copper atom.

2. Products according to claim 1, characterized in that in general formula (I), R represents a methoxy group, $R_1$, $R_2$ and $R_3$ represent a hydrogen atom and M represents a cobalt, nickel or copper atom.

3. Product according to claim 2, characterized in that M represents a cobalt atom.

4. Product according to claim 2, characterized in that M represents a nickel atom.

5. Product according to claim 2, characterized in that M represents a copper atom.

6. Product according to claim 1, characterized in that in general formula (I), R represents the methylthio radical, $R_1$, $R_2$ and $R_3$ represent a hydrogen atom and M represents a cobalt atom.

7. Product according to claim 1, characterized in that in general formula (I), R represents a $C_1$-$C_{18}$ alkoxyl or dialkylamino group, $R_1$ represents a hydrogen atom or a $C_1$–$C_{18}$ alkyl group, $R_2$ and $R_3$, identical or different, represent a hydrogen atom or a $C_1$–$C_{18}$ alkoxyl group and M represents a cobalt atom.

8. Product according to claim 7, characterized in that R represents a dimethylamino group, $R_1$, $R_2$ and $R_3$ represent a hydrogen atom.

9. Product according to claim 7, characterized in that R, $R_2$ and $R_3$ represent a methoxy group and $R_1$ represents a hydrogen atom.

10. Product according to claim 7, characterized in that R represents a methoxy group, $R_1$ represents a methyl group, $R_2$ and $R_3$ represent a hydrogen atom.

11. Product according to claim 1 characterized in that it is active in nonlinear optics.

12. The products having general formula (II)

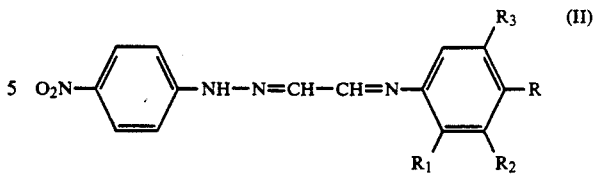

in which R represents a $C_1$–$C_{18}$ alkoxyl, $C_1$–$C_{18}$ alkylthio, $C_1$–$C_{18}$ monoalkylamino or $C_2$–$C_{36}$ dialkylamino group, $R_1$ represents a hydrogen atom or a $C_1$–$C_{36}$ alkyl group, $R_2$ and $R_3$, identical or different, represent a hydrogen atom or a $C_1$–$C_{18}$ alkoxyl group, with the exclusion of paranitrophenylhydrazono-1 paramethoxyphenylimino-2 ethane.

13. A derivative of formula (II) as defined in claim 12 which is paranitrophenylhydrazono-1 paramethylthiophenylimino-2 ethane.

14. A derivative of formula (II) as defined in claim 12 which is paranitrophenylhydrazono-1 paradimethylaminophenylimino-2 ethane.

15. A derivative of formula (II) as defined in claim 12 which is paranitrophenylhydrazono-1 (trimethoxy-3,4,5 phenyl) imino-2 ethane.

* * * * *

UNITED STATES PATENT AND TRADEMARK OFFICE
CERTIFICATE OF CORRECTION

PATENT NO. : 5,200,541
DATED : April 6, 1993
INVENTOR(S) : Thierry THAMI

It is certified that error appears in the above-identified patent and that said Letters Patent is hereby corrected as shown below:

On the title page: delete

"[*]  Notice:  The portion of the term of this patent subsequent to Dec. 17, 1992 has been disclaimed."

Signed and Sealed this

Seventh Day of December, 1993

Attest:

BRUCE LEHMAN

*Attesting Officer*    Commissioner of Patents and Trademarks